United States Patent
Fritz et al.

(10) Patent No.: US 9,012,577 B2
(45) Date of Patent: Apr. 21, 2015

(54) METHOD FOR PREPARING LINEAR ALPHA-OLEFINS WITH IMPROVED HEAT REMOVAL

(75) Inventors: Peter Fritz, Unterhaching (DE); Heinz Bölt, Wolfratshausen (DE); Karl-Heinz Hoffman, Germering (DE); Markus Köhler, München (DE); Hans-Jörg Zander, München (DE); Fuad Mosa, Riyadh (SA); Talal Ali, Riyadh (SA)

(73) Assignees: Saudi Basic Industries Corporation, Riyadh (SA); Linde AG (DE)

( * ) Notice: Subject to any disclaimer, the term of this patent is extended or adjusted under 35 U.S.C. 154(b) by 533 days.

(21) Appl. No.: 11/989,733

(22) PCT Filed: Jun. 13, 2006

(86) PCT No.: PCT/EP2006/005646
§ 371 (c)(1),
(2), (4) Date: Jan. 26, 2009

(87) PCT Pub. No.: WO2007/016996
PCT Pub. Date: Feb. 15, 2007

(65) Prior Publication Data
US 2009/0306312 A1    Dec. 10, 2009

(30) Foreign Application Priority Data
Jul. 29, 2005    (EP) .................................... 05016527

(51) Int. Cl.
*C08F 2/06*    (2006.01)
*C07C 2/30*    (2006.01)
*C07C 2/14*    (2006.01)

(52) U.S. Cl.
CPC ... *C07C 2/30* (2013.01); *C07C 2/14* (2013.01); C07C 2531/14 (2013.01)

(58) Field of Classification Search
USPC ......................................... 585/520, 522, 523
See application file for complete search history.

(56) References Cited

U.S. PATENT DOCUMENTS

| | | | |
|---|---|---|---|
| 2,351,123 A * | 6/1944 | Hays et al. ..................... | 585/330 |
| 5,496,783 A | 3/1996 | Chauvin et al. | |
| 5,811,608 A | 9/1998 | Stine et al. | |
| 5,811,619 A | 9/1998 | Commereuc et al. | |
| 5,817,905 A | 10/1998 | Commereuc et al. | |
| 6,221,986 B1 | 4/2001 | Commereuc et al. | |
| 6,737,555 B1 | 5/2004 | Maas et al. | |
| 2006/0063896 A1 * | 3/2006 | McElvain et al. ............... | 526/70 |

FOREIGN PATENT DOCUMENTS

| | | | | |
|---|---|---|---|---|
| CA | 2010850 C | | 8/1991 | |
| DE | 4338414 C1 * | | 3/1995 | ............ C08F 110/02 |
| JP | 2002256007 A | | 9/2002 | |
| WO | WO2004/029011 A1 | | 4/2004 | |
| WO | WO2004/029012 A1 | | 4/2004 | |
| WO | WO 2004029012 A1 * | | 4/2004 | ................ C07C 2/32 |

OTHER PUBLICATIONS

English translation of DE 4338414 C1.*
Lide, David R. Handbook of Chemistry and Physics, Section 3: Physical Constants of Organic Compounds, 89th Edition, p. 520.*
Lide, David R. Handbook of Chemistry and Physics, Section 3: Physical Constants of Organic Compounds, 2011. p. 520.*
Bolt, H.V. et al., "First Application of a New Process for Producing Linear Alpha-Olefins", Linde Technology Reports on Science and Technology, Dec. 2004, pp. 38-45.
Bassel W.D., "Preliminary Chemical Engineering Plant Design, Second Edition", 1990, p. 210, Van Nostrand Reinhold, New York, USA.
Extended European Search for Application No. 05016524.0; Date of Completion of the Search: Jan. 13, 2006; 5 pages.
International Search Report for International Application No. PCT/EP2006/05641; Mailing Date: Oct. 10, 2006; 2 pages.
Japanese Patent Publication No. 2002256007; Date of Publication: Sep. 11, 2002; Abstract Only, 1 page.
Written Opinion of the International Searching Authority for International Application No. PCT/EP2006/05641; Date of Mailing: Oct. 10, 2006; 6 pages.
Written Opinion of the International Searching Authority; International Application No. PCT/EP2006/005646; International Filing Date: Jun. 13, 2006; Date of Mailing: Sep. 10, 2006; 2 pages.
International Preliminary Report of the International Searching Authority; International Application No. PCT/EP2006/005646; International Filing Date: Jun. 13, 2005; Date of Mailing: Sep. 10, 2006; 2 pages.

* cited by examiner

*Primary Examiner* — Ling Choi
*Assistant Examiner* — Catherine S Branch
(74) *Attorney, Agent, or Firm* — Cantor Colburn LLP

(57) ABSTRACT

The present invention relates to a method for preparing linear alpha-olefins by oligomerizing of ethylene in the presence of a first organic solvent and a homogenous catalyst in a reactor, characterized in that the reactor overhead is cooled by means of a refrigerant.

9 Claims, No Drawings

METHOD FOR PREPARING LINEAR ALPHA-OLEFINS WITH IMPROVED HEAT REMOVAL

The present invention relates to a method for preparing linear alpha-olefins (LAO) by oligomerizing of ethylene in the presence of a first organic solvent and a homogenous catalyst in a reactor.

The oligomerization of ethylene using an organometallic catalyst is widely known in the art. The oligomerization is highly exothermic so that reaction heat has to be removed from the reactor to prevent a runaway.

DE 43 38 414 C1 discloses a method for the preparation of linear alpha-olefins, wherein polymer grade ethylene is re-circulated to remove the reaction heat. Therefore, ethylene feed (having an ethylene content of approximately 100% with minor amounts of impurities) is introduced into the reactor at a lower temperature, and non-oligomerized monomeric ethylene is removed at a higher temperature, cooled down and re-introduced into the reactor.

It was found that only about 3% of the ethylene feed is used in the oligomerization process, wherein the remainder is utilized as cooling media. Ethylene is quite expensive.

Additionally, it was found that for sufficient heat removal the ethylene cooling cycle gas flow rate has to be sufficiently high resulting in increased demands for equipment, piping, power consumption, etc.

According to the state of the art, a typical overhead temperature of a reactor for the oligomerization of ethylene to produce linear alpha-olefins is about 50° C., whereas the bottom temperature of the reactor is about 60 to about 100° C. In this case, the cooling of the overhead is usually achieved by means of cooling water, preferably utilizing a condenser. Based on these conditions and the application of toluene as suitable solvent, a small amount of toluene is evaporized at reactor bottoms, flows upwards to the reactor overhead, is partly condensed and serves as internal reflux. This internal cycle contributes to the heat removal from the reactor only with a very small percentage.

It is therefore an object of the present invention to provide a method for preparing linear alpha-olefins by oligomerizing of ethylene which method overcomes the disadvantages of the prior art. Especially, a method shall be provided showing an improved heat removal from the reactor, together with a significant reduction of cooling cycle gas flow rate, resulting in savings for equipment, piping, power consumption, etc.

This object is achieved in that the reactor overhead temperature is cooled by means of a refrigerant.

Preferably, the temperature in the reactor overhead is held at about 15 to about 20° C., preferably by a condenser.

More preferably, the refrigerant is propylene.

Additionally, the method may be carried out in the presence of at least one cooling medium added to the reactor and condensing at the top of the reactor and re-evaporating at reactor bottoms.

Preferably, the cooling medium is selected so that it substantially remains within the reactor while operating the method.

In one also preferred embodiment, the cooling medium is selected from an inert second organic solvent having a boiling point of at least about 120° C. at atmospheric pressure.

The first organic solvent may be toluene.

Preferably, the catalyst comprises a zirconium salt of organic acids and at least one organoaluminum compound.

It is proposed that the zirconium salt has the formula $ZrCl_{4-m} X_m$, wherein X=OCOR or $OSO_3R'$ with R and R' being independently alkyl, alkene or phenyl, and wherein $0<m<4$.

The at least one aluminum compound may be $Al(C_2H_5)_3$, $Al_2Cl_3(C_2H_5)_3$, $AlCl(C_2H_5)_2$ or mixtures thereof.

Finally, the bottom temperature of the oligomerization reactor is between about 60 to about 100° C.

Surprisingly, it was found that cooling of the reactor overhead by means of a refrigerant, preferably by a reduction of the reactor overhead temperature to about 15 to about 20° C. significantly increases the internal cooling cycle. Additionally, the high ethylene feed being so far essential for heat removal, can be reduced, and thus the cooling cycle gas flow rate can be significantly reduced. This further results in savings for equipment, piping, power consumption, etc.

In a preferred embodiment, an appropriate cooling medium can be further introduced into the LAO reactor providing a further improved removal of the heat generated due to the exothermic oligomerization process. The cooling medium which is to be introduced into the reactor, preferably injected, is selected so that the cooling medium may easily condensate at the top of the reactor, but may be also easily re-evaporated at reactor bottoms. Further, the boiling point at atmospheric pressure of the cooling medium is preferably selected in that it satisfactorily avoids the discharge of the cooling medium from the reactor.

According to the inventive method a direct internal cooling may be achieved.

The method of the present invention is now illustrated in detail.

Catalyst dissolved in a suitable solvent, such as toluene, is fed to an oligomerization reactor. Additionally, ethylene is supplied to the reactor, and a cooling medium may be also provided for introduction therein. The cooling medium is selected so that it may easily condensate at the top of the reactor, but may be also easily re-evaporated at reactor bottoms. In the reactor, ethylene is oligomerized to obtain linear alpha-olefins. Especially, the oligomerization of ethylene is conducted in the reactor, when the feed of ethylene bubbles through the mixture of solvent and catalyst. The products of the oligomerization remain dissolved in the solvent. The temperature of the reactor bottom is about 60 to about 100° C.

The temperature of the reactor overhead is held at about 15 to about 20° C., preferably by application of a refrigerant, preferably utilizing a condenser. In this matter, the internal cooling cycle within the reactor is significantly increased. From the reactor, a mixture of ethylene and light alpha-olefins may be removed via the reactor overhead and may be collected in a separator. The liquid obtained, comprising solvent and alpha-olefins, may be re-circulated into the reactor. The part from the separator remaining gaseous may be further cooled in a cooling device to a temperature of about 5° C. and is then transferred into a second separator. In the cooling device the cooling is adjusted so that olefins heavier than ethylene are liquefied. The linear alpha-olefins obtained may then be further processed as is known in the art. Non-consumed ethylene may be, in admixture with a fresh feed thereof, again introduced into the reactor. A liquid mixture comprising solvent, catalyst and linear alpha-olefins may be discharged from the reactor via a line above the reactor bottom and may be further processed as known in the art.

The features disclosed in the foregoing description, in the drawing or in the claims may, both separately and in any combination thereof, be material for realizing the invention in diverse forms thereof.

The invention claimed is:

1. A method for preparing linear alpha-olefins by oligomerizing of ethylene in the presence of an organic solvent and a homogenous catalyst in a reactor, characterized in that the reactor bottoms temperature is between about 60° C. to about 100° C. and the reactor overhead comprising alpha-olefin and the organic solvent is cooled to about 15° C. to about 20° C. to produce a condensate which is re-circulated into the reactor.

2. The method according to claim 1, wherein the reactor overhead is cooled in a condenser by a refrigerant and wherein the refrigerant is propylene.

3. The method according to claim 1, wherein the method is carried out in the presence of at least one cooling medium added to the reactor at the top of the reactor and vaporizes in the reactor bottoms.

4. The method according to claim 3, wherein the cooling medium remains within the reactor during said method.

5. The method according to claim 4, wherein the cooling medium is an inert second organic solvent having a boiling point of at least about 120° C. at atmospheric pressure.

6. The method of claim 1, wherein the organic solvent is toluene.

7. The method according to claim 6, wherein the catalyst comprises a zirconium salt of organic acids and at least one organoaluminum compound.

8. The method according to claim 7, wherein the zirconium salt has the formula $ZrCl_{4-m}X_m$, wherein $X=OCOR$ or $OSO_3R'$ with R and R' being independently alkyl, alkene or phenyl, and $0<m<4$.

9. The method according to claim 8, wherein the at least one aluminum compound is $Al(C_2H_5)_3$, $Al_2Cl_3(C_2H_5)_2$, $AlCl(C_2H_5)_2$ or mixtures thereof.

\* \* \* \* \*